(12) United States Patent
Herve et al.

(10) Patent No.: US 11,592,435 B2
(45) Date of Patent: Feb. 28, 2023

(54) METHOD FOR OBSERVING A SAMPLE

(71) Applicant: Commissariat A L'Energie Atomique et aux Energies Alternatives, Paris (FR)

(72) Inventors: Lionel Herve, Corenc (FR); Cedric Allier, Grenoble (FR)

(73) Assignee: Commissariat A L'Energie Atomique et aux Energies Alternatives, Paris (FR)

( * ) Notice: Subject to any disclaimer, the term of this patent is extended or adjusted under 35 U.S.C. 154(b) by 601 days.

(21) Appl. No.: 16/655,300

(22) Filed: Oct. 17, 2019

(65) Prior Publication Data

US 2020/0124586 A1  Apr. 23, 2020

(30) Foreign Application Priority Data

Oct. 17, 2018 (FR) ...................................... 18 59618

(51) Int. Cl.
  *G01N 33/483* (2006.01)
  *G01N 15/14* (2006.01)
  (Continued)

(52) U.S. Cl.
  CPC ..... *G01N 33/4833* (2013.01); *G01N 15/1434* (2013.01); *G03H 1/0443* (2013.01); *G01N 2201/12* (2013.01); *G03H 2001/0033* (2013.01)

(58) Field of Classification Search
  CPC ........... G01N 2015/1454; G01N 21/89; G01N 21/8983; G01N 15/1475; G01N 21/956;
  (Continued)

(56) References Cited

U.S. PATENT DOCUMENTS

2014/0263963 A1 * 9/2014 Broxton ............. G02B 27/0075
                                                                        250/208.1
2017/0059468 A1   3/2017 Yevick et al.
(Continued)

FOREIGN PATENT DOCUMENTS

EP    3199941 A1 *  8/2017    ........... G01N 21/255
EP    3270232 A1 *  1/2018    ........... G03H 1/0404
(Continued)

OTHER PUBLICATIONS

French Preliminary Search Report dated Apr. 16, 2019 in French Application 18 59618 filed on Oct. 17, 2018 (with English Translation of Categories of Cited Documents & Written Opinion).
(Continued)

*Primary Examiner* — Michael P Stafira
(74) *Attorney, Agent, or Firm* — Oblon, McClelland, Maier & Neustadt, L.L.P.

(57) ABSTRACT

A method for observing a sample (10), the sample lying in a plane of the sample defining radial coordinates, the method comprising the following steps:
  a) illuminating the sample using a light source (11), able to emit an incident light wave (12) that propagates toward the sample along a propagation axis (Z);
  b) acquiring, using an image sensor (16), an image ($I_0$) of the sample (10), said image being formed in a detection plane ($P_0$), the sample being placed between the light source (11) and the image sensor (16), such that the incident light wave sees an optical path difference, parallel to the propagation axis (Z), by passing through the sample;
  c) processing the image acquired by the image sensor;
wherein the processing of the acquired image comprises taking into account vectors of parameters, respectively defined at a plurality of radial coordinates, in the plane of the sample, each vector of parameters being associated with one
(Continued)

radial coordinate, and comprising a term representative of an optical parameter of the sample, at least one optical parameter being an optical path difference induced by the sample at the radial coordinate, the vectors of parameters describing the sample.

14 Claims, 6 Drawing Sheets

(51) Int. Cl.
*G03H 1/04* (2006.01)
*G03H 1/00* (2006.01)

(58) Field of Classification Search
CPC .......... G01N 15/1434; G01N 15/1468; G01N 2021/8883; G01N 21/8806; G01N 21/9501; G01N 2201/12; G01N 33/4833; G01N 15/0205; G01N 21/21; G01N 2015/1006; G01N 2015/1488; G01N 21/95607; G01N 2223/419; G01N 2223/612; G01N 2510/00; G01N 15/1463; G01N 21/453; G01N 15/1429; G01N 2015/144; G01N 21/4788; G01N 15/205; G01N 2015/0233; G01N 21/255; G01N 2015/1486; G01N 33/49; G01N 21/455; G01N 2201/0627; G01N 2021/1772; G01N 15/0211; G01N 15/0227; G01N 2015/0238; G01N 2015/035; G01N 15/1431; G01N 15/1459; G01N 2015/0065; G01N 2015/1445; G01N 2021/1782; G01N 21/27; G01N 21/51; G01N 2015/008; G01N 2015/0084; G01N 21/95623; G03H 1/0443; G03H 1/0866; G03H 2001/0447; G03H 2001/0452; G03H 2001/0816; G03H 1/0005; G03H 2001/0033; G03H 2001/005; G03H 2001/0471; G03H 2001/0875; G03H 2210/55; G03H 2222/18; G03H 1/0248; G03H 1/202; G03H 1/26; G03H 1/265; G03H 2001/2675; G03H 2001/0883; G03H 2001/0454; G03H 1/0465; G03H 2222/13; G03H 1/0011; G03H 1/041; G03H 1/22; G03H 2222/12; G03H 2227/03; G03H 1/2645; G03H 2001/2247; G03H 2001/2268; G03H 2001/045; G03H 2226/11; G03H 2001/0825; G03H 2226/02; G03H 1/0891; G03H 1/16; G03H 2001/0458; G03H 2001/046; G03H 2001/2263; G03H 2001/266; G03H 2210/13; G03H 2210/441; G03H 2210/62; G03H 2222/16; G03H 2222/17; G03H 2222/22; G03H 2222/36; G03H 2223/12; G03H 2223/13; G03H 2240/56; G03H 2240/62; G03H 1/04; G03H 1/0402; G03H 1/08; G03H 1/0841; G03H 1/12; G03H 1/2294; G03H 1/34; G03H 2001/0434; G03H 2001/0858; G03H 2223/14; G03H 2223/23; G03H 2240/53

See application file for complete search history.

(56) References Cited

U.S. PATENT DOCUMENTS

2017/0212343 A1* 7/2017 Morel .................. G03H 1/0005
2018/0341099 A1 11/2018 Morel et al.

FOREIGN PATENT DOCUMENTS

| FR | 3029632 A1 | * | 6/2016 | ......... G01N 15/1434 |
|----|------------|---|--------|------------------------|
| FR | 3043205 A1 | * | 5/2017 | ............. G01N 15/00 |
| FR | 3047077 A1 | * | 7/2017 | ........... G01N 21/255 |
| FR | 3049348 A1 | * | 9/2017 | ......... G01N 15/0205 |
| WO | WO-2016091749 A1 | * | 6/2016 | ......... G01N 15/1434 |
| WO | WO-2017077238 A1 | * | 5/2017 | ............. G01N 15/00 |
| WO | WO-2017162985 A1 | * | 9/2017 | ......... G01N 15/1429 |

OTHER PUBLICATIONS

Olivier, T, et al., "Optimizing phase object reconstruction using an in-line digital holographic microscope and a reconstruction based on a Lorenz-Mie model", Proceedings of SPIE, vol. 10677, 2018, 11 pages.

Krishnatreya, B, et al., "Measuring Boltzmann's constant through holographic video microscopy of a single colloidal sphere", American Journal of Physics, vol. 82, No. 1, 2014, pp. 23-31.

* cited by examiner

METHOD FOR OBSERVING A SAMPLE

TECHNICAL FIELD

The technical field of the invention is related to the observation of a sample, in particular a biological sample, by lensless imaging, employing a holographic reconstruction algorithm of improved performance.

PRIOR ART

The observation of samples, and in particular biological samples, by lensless imaging has seen substantial development over the last ten years. This technique allows a sample to be observed by placing it between a light source and an image sensor, without placing any optically magnifying lenses between the sample and the image sensor. Thus, the image sensor collects an image of the light wave transmitted by the sample.

This image is formed of interference patterns generated by interference between the light wave emitted by the light source and transmitted by the sample, and diffracted waves resulting from the diffraction, by the sample, of the light wave emitted by the light source. These interference patterns are sometimes called diffraction patterns.

Document WO2008090330 describes a device allowing biological samples, in fact cells, to be observed by lensless imaging. The device allows an interference pattern the morphology of which allows the type of cell to be identified to be associated with each cell. Lensless imaging would thus appear to be a simple and inexpensive alternative to a conventional microscope. In addition, its field of observation is clearly much larger than it is possible for that of a microscope to be. It will thus be understood that the prospective applications related to this technology are many and various.

Generally, the image formed on the image sensor, containing the interference patterns, may be processed using a holographic reconstruction algorithm, so as to estimate optical properties of the sample, for example a transmission coefficient or a phase. Such algorithms are well known in the field of holographic reconstruction. To do this, the distance between the sample and the image sensor being known, a propagation algorithm, taking into account this distance, and the wavelength of the light wave emitted by the light source, is applied. It is then possible to reconstruct an image of an optical property of the sample. The reconstructed image may, in particular, be a complex image of the light wave transmitted by the sample, containing information on the optical properties with respect to the absorption of or phase variation in the sample. However, holographic reconstruction algorithms may induce reconstruction noise in the reconstructed image, which noise is referred to as "twin images". This is essentially due to the fact that the image formed on the image sensor contains no information on the phase of the light wave reaching this sensor. Thus, the holographic reconstruction is carried out on the basis of partial optical information, based solely on the intensity of the light wave collected by the image sensor.

The improvement of holographic reconstruction quality has been the subject of many developments, employing algorithms that are frequently called "phase retrieval" algorithms, allowing the phase of the light wave to which the image is exposed to be estimated.

A numerical reconstruction algorithm is for example described in US2012/0218379. Reconstruction algorithms have also been described in WO2016189257 or in WO2017162985.

The inventors propose a method for observing a sample using a holographic imaging method, the method comprising a step of reconstructing a complex image of the sample, on the basis of which image it is possible to obtain a spatial representation of parameters of the sample.

SUMMARY OF THE INVENTION

A first subject of the invention is a method for observing a sample, the sample lying in a plane of the sample defining radial coordinates, the method comprising the following steps:
  a) illuminating the sample using a light source, configured to emit an incident light wave that propagates toward the sample along a propagation axis;
  b) acquiring, using an image sensor, an image of the sample, said image being formed in a detection plane, the sample being placed between the light source and the image sensor, such that the incident light wave sees an optical path difference, parallel to the propagation axis, by passing through the sample;
  c) processing the image acquired by the image sensor;
wherein the processing of the acquired image comprises the following iterative steps:
  i) taking into account a set of vectors of parameters, describing the sample, and respectively defined at a plurality of radial coordinates, in the plane of the sample, each vector of parameters being associated with one radial coordinate, and comprising a term representative of an optical parameter of the sample, at least one optical parameter being an optical path difference induced by the sample at each radial coordinate;
  ii) on the basis of the vectors of parameters, forming a complex image of the sample in the plane of the sample;
  iii) applying a propagation operator to the complex image of the sample formed in the plane of the sample, in order to compute an image of the sample in the detection plane;
  iv) comparing the image acquired in step b) and the image computed in step iii), in order to compute a validity indicator;
  v) updating all of the vectors of parameters, so as to make the validity indicator tend toward a preset value;
  vi) reiterating steps ii) to v) taking into account the vectors of parameters estimated in step v).

Step v) may further comprise determining a gradient of the validity indicator as a function of at least one parameter, such that the vectors of parameters are updated in order to decrease the validity indicator of the following iteration.

Step v) may comprise implementing of an algorithm of gradient-descent type.

Each parameter vector may comprise:
at least one optical parameter representative of an optical path difference along the propagation axis;
an optical parameter representative of absorbance.

Each parameter vector may comprise:
taking into account a morphological constraint of the sample;
computing a morphological criterion from the vectors of parameters, the morphological criterion quantifying a deviation of the vectors of parameters, describing the sample, with respect to the morphological constraint of the sample, such that the validity indicator is obtained from a combination:
- of an error criterion, determined from a comparison between the image acquired in b) and the image obtained in iii);
- and of the morphological criterion.

The validity indicator may be an optionally weighted sum of the error criterion and of the morphological criterion. The validity indicator may be a weighted sum of the error criterion and of the morphological criterion, the weighting varying between at least two successive iterations.

According to on embodiment:
- in b), acquiring an image of the sample in various spectral bands;
- each vector of parameters comprises at least one optical parameter defined in one of the spectral bands;
- in iii), the complex image of the sample is propagated for each spectral band, so as to compute, for each spectral band, an image of the sample
- iv) comprises comparing, for each spectral band, the image computed in iii) and the image acquired in b); so that the validity indicator computed in iv) is computed on the basis of the comparisons made in iv).

In first iterations, an optical parameter may be considered to not vary as a function of the spectral band. Beyond first iterations, the optical parameter may be considered to be variable as a function of the spectral band.

In step iii), the computation of the image of the sample in the detection plane may comprise applying a convolution with a convolution kernel, the convolution kernel representing a spatial extent of the light source.

In step iii), the computation of the image in the detection plane may comprise an integral of an elementary image, defined in an elementary spectral band, the integral being computed to take into account an emission spectral band of the light source. The emission spectral band is then formed by a juxtaposition of various elementary spectral bands. In other words, each elementary spectral band forms the spectral band.

Other advantages and features will become more clearly apparent from the following description of particular embodiments of the invention, which are given by way of nonlimiting example, and shown in the figures listed below.

FIGURES

DESCRIPTION OF PARTICULAR EMBODIMENTS

Figure 1A:
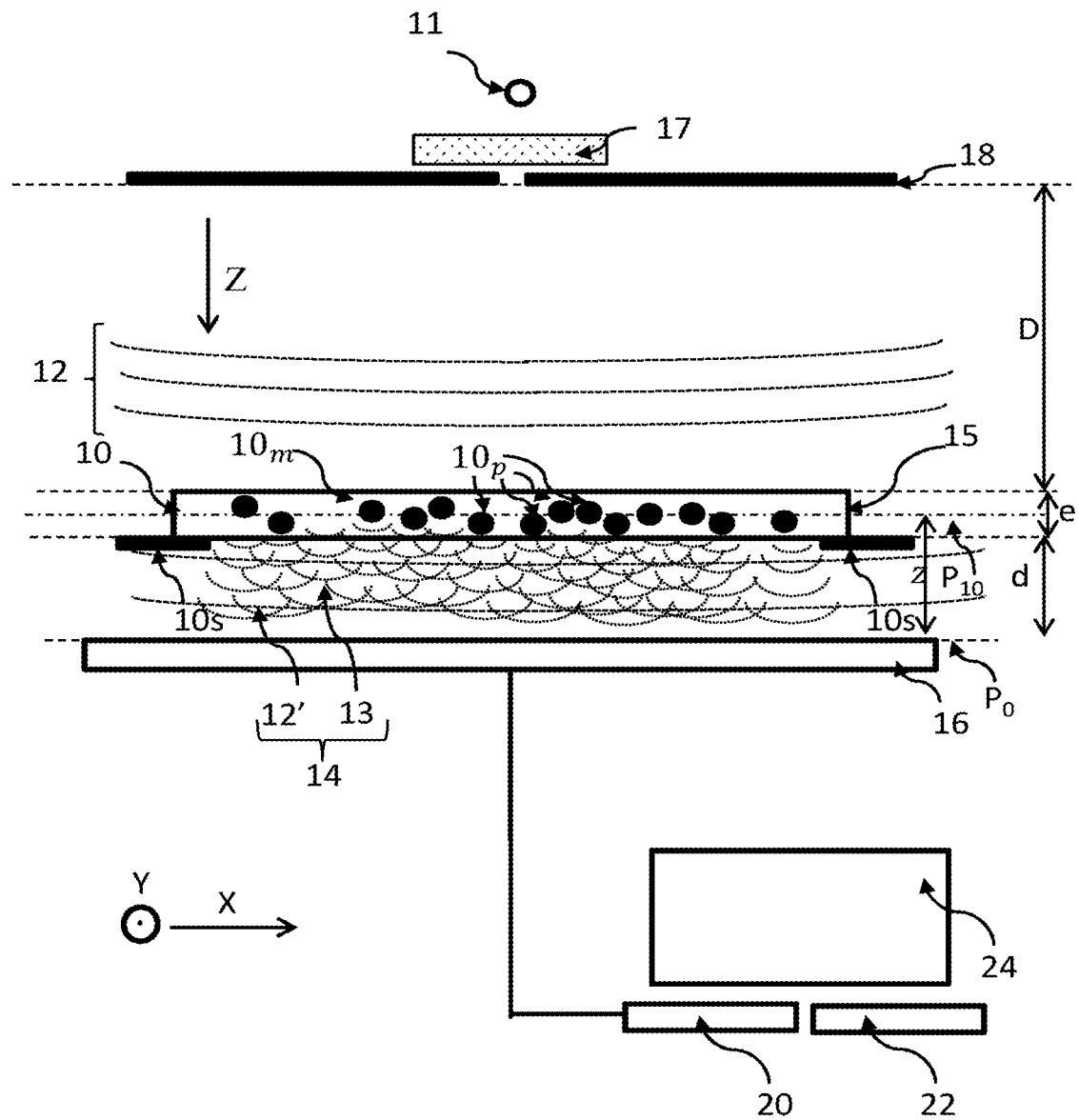
FIG. 1A shows a device allowing the invention to be implemented.

FIG. 1A shows an example of a device according to the invention. A light source 11 is configured to emit a light wave 12, called the incident light wave, which propagates in the direction of a sample 10, along a propagation axis Z. The light wave is emitted in a spectral band $\Delta\lambda$, comprising a wavelength $\lambda$. This wavelength may be a central wavelength of said spectral band.

Figure 1B:
FIG. 1B shows an example light source able to be used in the device of FIG. 1A.

According to one embodiment, the light source 11 comprises elementary light sources $11_j$. The index j designates the index of the elementary light source. Each light source emits a light wave, along the propagation axis Z, in a spectral band $\Delta\lambda_j$. It is for example possible to use a light source 11 comprising three elementary light sources $11_1$, $11_2$, $11_3$ as shown in FIG. 1B. The elementary sources emit in spectral bands that are different from one another, for example in the blue, in the green and in the red. Such a light source has been described in WO2016189257.

The sample 10 is a sample that it is to be characterized. It may notably be a question of a medium $10m$ containing particles $10p$. The particles $10p$ may be blood particles, and for example red blood cells. It may also be a question of cells, microorganisms, for example bacteria or yeast, microalgae, micro-spheres, or droplets that are insoluble in the liquid medium, lipid nanoparticles for example. Preferably, the particles $10p$ have a diameter, or are inscribed in a diameter, smaller than 1 mm, and preferably smaller than 100 μm. It is a question of microparticles (diameter smaller than 1 mm) or of nanoparticles (diameter smaller than 1 μm). The medium $10m$, in which the particles bathe, may be a liquid medium, for example a liquid phase of a bodily liquid, a culture medium or a liquid sampled from the environment or from an industrial process. It may also be a question of a solid medium or a medium having the consistency of a gel, for example an agar substrate, which is propitious to the growth of bacterial colonies.

The sample may also be a solid sample, for example a thin slide of biological tissue, such as a pathology slide, or a dry content of a fluid, for example a biological fluid.

The sample is preferably transparent or sufficiently translucent to be able to allow an image to be formed with the image sensor.

In this example, the sample 10 is contained in a fluidic chamber 15. The fluidic chamber 15 is for example a micro-cuvette, commonly used in point-of-care type devices, into which the sample 10 penetrates, for example by capillary action. The thickness e of the sample 10, along the propagation axis, typically varies between 20 μm and 1 cm, and is preferably comprised between 50 μm and 500 μm, and is for example 150 μm.

The sample lies in a plane $P_{10}$, called the plane of the sample, perpendicular to the propagation axis. It is held on a holder $10s$. The plane of the sample is defined by two orthogonal axes X and Y, respectively defining coordinates x and y. Each pair of coordinates (x,y) corresponds to one radial coordinate r. The radial coordinates are defined in the plane of the sample and in a detection plane that is described below.

The distance D between the light source 11 and the sample 10 is preferably larger than 1 cm. It is preferably comprised between 2 and 30 cm. Preferably, the light source, seen by the sample, may be considered to be point-like. This means that its diameter (or its diagonal) is preferably smaller than one tenth, better still one hundredth of the distance between the sample and the light source. Thus, preferably, the light source reaches the sample in the form of plane waves, or waves that may be considered as such.

The light source 11 may be a light-emitting diode or a laser diode. It may be associated with a diaphragm 18, or spatial filter. The aperture of the diaphragm is typically comprised between 5 µm and 1 mm, and preferably between 50 µm and 500 µm. In this example, the diaphragm is that supplied by Thorlabs under the reference P150S and its diameter is 150 µm. The diaphragm may be replaced by an optical fiber, a first end of which is placed facing the light source 11 and a second end of which is placed facing the sample 10.

The device preferably comprises a diffuser 17, placed between the light source 11 and the diaphragm 18. The use of such a diffuser allows constraints on the centrality of the light source 11 with respect to the aperture of the diaphragm 18 to be relaxed. The function of such a diffuser is to distribute the light beam, produced by the elementary light source 11, in a cone of angle α, α being equal to 30° in the present case. Preferably, the scattering angle α varies between 10° and 80°.

Preferably, the emission spectral band Δλ of the incident light wave 12 has a width smaller than 100 nm. By spectral bandwidth what is meant is a fullwidth at half maximum of said spectral band. In the rest of the text, each spectral band is designated by a wavelength λ representative of the spectral band, for example the central wavelength.

The sample 10 is placed between the light source 11 and an image sensor 16. The latter preferably lies parallel, or substantially parallel, to the plane in which the sample lies. The term substantially parallel means that the two elements may not be rigorously parallel, an angular tolerance of a few degrees, smaller than 20° or 10° being acceptable.

The image sensor 16 is able to form an image in a detection plane $P_0$. In the example shown, it is a question of a CCD or CMOS image sensor comprising a matrix array of pixels. CMOS sensors are the preferred sensors because the size of the pixels is smaller, this allowing images the spatial resolution of which is more favorable to be acquired. The detection plane $P_0$ preferably lies perpendicular to the propagation axis Z of the incident light wave 12. Thus, the detection plane $P_0$ is parallel to the plane of the sample $P_{10}$. The image sensor comprises pixels, one radial coordinate r being associated with each pixel.

The distance d between the sample 10 and the matrix array of pixels of the image sensor 16 is preferably comprised between 50 µm and 2 cm, and more preferably comprised between 100 µm and 2 mm.

In the device shown in FIG. 1A, the absence of magnifying or image-forming optic between the image sensor 16 and the sample 10 will be noted. This does not prevent focusing micro-lenses optionally being present level with each pixel of the image sensor 16, said micro-lenses not having the function of magnifying the image acquired by the image sensor.

Under the effect of the incident light wave 12, the sample 10 may generate a diffracted wave, liable to produce, in the detection plane $P_0$, interference, in particular with a portion of the incident light wave 12 transmitted by the sample. Moreover, the sample may absorb one portion of the incident light wave 12. Thus, the light wave 14, transmitted by the sample, and to which the image sensor 16 is exposed, is formed following absorption and diffraction of the incident light wave 12 by the sample. Thus, the sample results in absorption of one portion of the incident light wave, and in a phase shift of the latter. The phase shift is due to a variation in refractive index (or optical index) when the light wave 14 propagates through the sample.

The light wave 14 may also be designated by the term exposure light wave. A processor 20, for example a microprocessor, is able to process each image acquired by the image sensor 16. In particular, the processor is a microprocessor connected to a programmable memory 22 in which a sequence of instructions for carrying out the image-processing and computing operations described in this description is stored. The processor may be coupled to a screen 24 allowing images acquired by the image sensor 16 or computed by the processor 20 to be displayed.

The image acquired by the image sensor forms a hologram. It generally does not allow a satisfactory visual representation of the sample, in particular when the sample comprises diffracting elements that are very close to one another. This is notably the case when the sample contains particles that are very close to one another, or when the sample is a thin slide of biological tissue. In order to obtain a satisfactory observation of the sample, iterative image-reconstruction algorithms have been developed, such as those described with reference to the prior art. These algorithms comprise iteratively applying a holographic propagation operator, so as to propagate the hologram formed in the detection plane to a reconstruction plane, the latter generally corresponding to a plane of the sample, i.e. the plane in which the sample lies. The plane of the sample is generally parallel to the detection plane. The algorithms described in the prior art successively propagate/back-propagate images between the detection plane and the plane of the sample. The image acquired by the image sensor contains no information relating to the phase of the exposure light wave. The objective of these algorithms is to estimate, iteratively, the phase of the exposure light wave in the detection plane. This allows a correct image of the sample in the reconstruction plane to be formed. Thus, these algorithms allow optical properties of the exposure light wave 14 to be obtained. It may for example be a question of the modulus or phase.

The approach proposed by the inventor is different, since it aims not to obtain properties of the exposure light wave 14, but properties of the sample itself, and notably optical properties of the latter. To do this, the sample is described by vectors F(r), each vector being defined at a radial coordinate r in the plane of the sample. Each term of each vector corresponds to one optical property of the sample.

The inventor believes that an important property to consider is an optical path difference induced by the sample, along the propagation axis Z. To do this, radial coordinates r=(x,y), defined in the plane of the sample, are considered. At each radial coordinate r, a vector of parameters F(r) describing the sample is defined. The vector of parameters F(r) is of size $(1, N_w)$, where $N_w$ is the number of parameters in question. Each component of the vector of parameters is an optical parameter of the sample.

Figure 2:
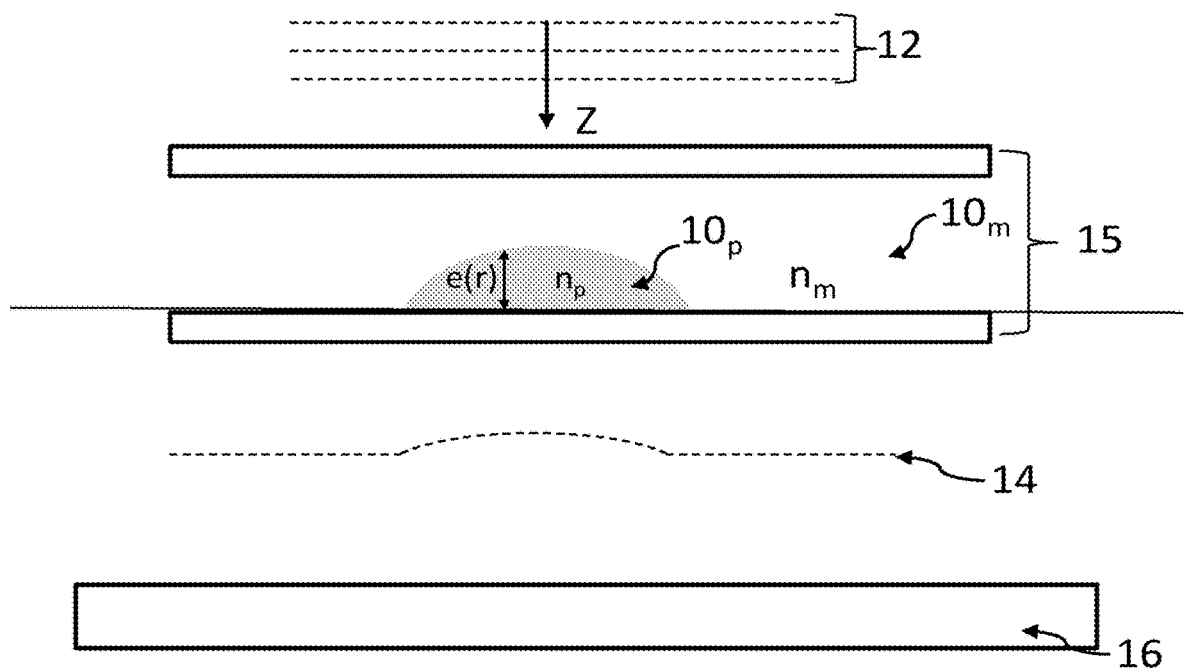
FIG. 2 shows the evolution of a light wave and illustrates the delay induced by an optical path difference. The delay generates a phase shift in the light wave.

One component of the vector is an optical path difference L(r) induced by the sample in a direction parallel to the propagation axis Z. FIG. 2 shows a detail of a particle $10_p$ of the sample. In this example, the particle $10_p$ is an adherent cell. It adheres to a transparent wall of the fluidic chamber 15. The particle $10_p$ has a refractive index $n_p$, whereas the medium $10m$ in which it bathes has a refractive index $n_m$.

At each radial coordinate r, the optical path difference L(r) produced by the particle is such that $L(r)=(n_p-n_m) \times e(r)$ where e(r): thickness of the particle at the radial coordinate r and x is the multiplication operator.

In FIG. 2, the wave front of the light wave 12 incident on the sample, and of the exposure light wave 14 to which the image sensor 16 is exposed, the exposure light wave propagating from the sample to the image sensor, have been represented by dashed lines. In this example, $n_p > n_m$. The wave front is plane before reaching the sample. Downstream of the sample, the wave front is deformed because of the appearance of optical path differences induced by the particle.

Another component of the vector F(r) may be an absorbance α(r) of the sample. When the light source 11 comprises various elementary light sources $11_j$, the optical path and the absorbance may be expressed for each wavelength λ.

Let $A_{10}$ be the complex amplitude of the exposure light wave 14 in the plane of the sample $P_{10}$. At each radial coordinate r, the complex amplitude $A_{10}(r)$ may be defined from the vector of parameters F(r), depending on assumptions established a priori:

either the sample may be considered to be transparent, in which case the absorbance α is zero and $$A_{10}^\lambda(r) = b^\lambda(r)\exp\left(2i\pi\frac{L(r)}{\lambda}\right). \quad (1)$$

The index λ designates a wavelength and $i^2=1$. As indicated above, λ is the central wavelength of an emission spectral band Δλ. The term $b^\lambda$ is an amplitude representative of the incident light wave 12 reaching the sample. This amplitude may be measured by the image sensor 16 in the absence of sample 10 on the holder 10s. The light source 11 then directly illuminates the image sensor. From the image $I_{0,b}^\lambda(r)$ acquired by the image sensor 16 in the emission spectral band Δλ, the amplitude $b^\lambda$ is obtained using $b^\lambda(r)=\sqrt{I_{0,b}^\lambda(r)}$. (1)

or the sample has a nonzero absorbance, in which case:

$$A_{10}^\lambda(r) = b^\lambda(r)\exp\left(2i\pi\frac{L(r)}{\lambda} + \alpha^\lambda(r)\right), \quad (2)$$

where $\alpha^\lambda(r)$ is the absorbance in the spectral band λ of the radial coordinate r.

It is possible to consider the optical path difference L(r) to depend on the emission spectral band, in which case it is denoted $L^\lambda(r)$. In this case, the complex amplitude in the plane of the sample is written:

$$A_{10}^\lambda(r) = b^\lambda(r)\exp\left(2i\pi\frac{L^\lambda(r)}{\lambda}\right) \text{ or} \quad (3)$$

$$A_{10}^\lambda(r) = b^\lambda(r)\exp\left(2i\pi\frac{L^\lambda(r)}{\lambda} + \alpha^\lambda(r)\right) \quad (4)$$

when the absorbance is considered to be zero or nonzero, respectively.

In one configuration a fitting variable defining a phase jump is defined. Specifically, the phase of a light wave is defined modulo 2π. It is possible to define an integer $N_\varphi$, allowing a quantitative phase value to be obtained, such that:

$$A_{10}^\lambda(r) = b^\lambda(r)\exp\left(2i\pi\frac{L(r) - N_\varphi\left(1 - \frac{\lambda}{\lambda_0}\right)}{\lambda} + \alpha^\lambda(r)\right) \quad (5)$$

where $\lambda_0$ is a central wavelength of one of the spectral bands used.

Each vector F(r) contains $N_w$ terms $F_w(r)$ with $1 \leq w \leq N_w$. Depending on the expression of the amplitude taken into account, the vector of parameters F(r) may vary:

When the expression in question is expression (1), F(r) may contain only L(r).

When the expression in question is expression (2), F(r) may contain L(r) and the absorbance $\alpha^\lambda(r)$ in each illumination spectral band. When there are three illumination spectral bands, F(r) contains $N_w=4$ terms.

When the expression in question is expression (3), F(r) may contain $L^\lambda(r)$ in each illumination spectral band. When there are three illumination spectral bands, F(r) contains $N_w=3$ terms.

When the expression in question is expression (4), F(r) may contain $L^\lambda(r)$ and the absorbance $\alpha^\lambda(r)$ in each illumination spectral band. When there are three illumination spectral bands, F(r) contains $N_w=6$ terms.

When the expression in question is expression (5), F(r) may contain L(r) and the absorbance $\alpha^\lambda(r)$ in each illumination spectral band and the integer $N_\varphi$. F(r) contains $N_w=5$ terms.

Figure 3:
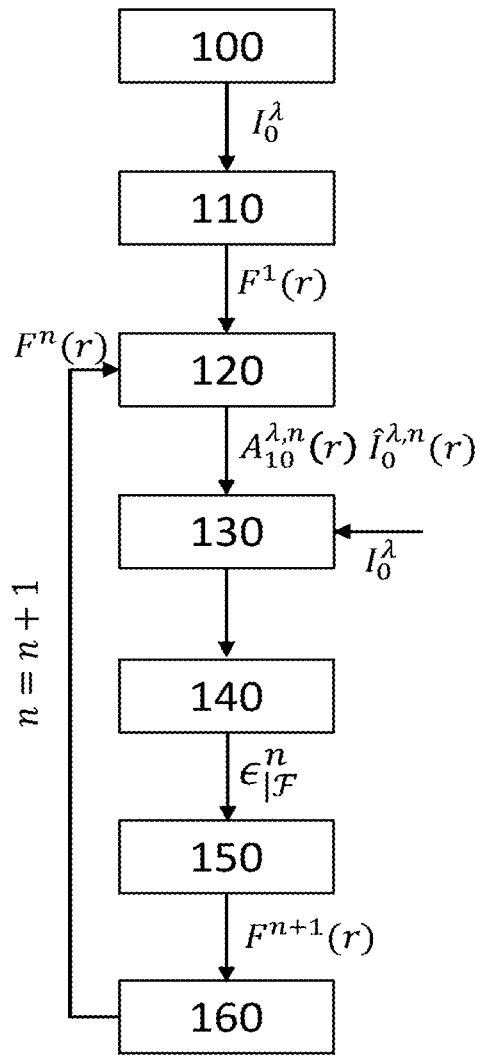
FIG. 3 shows the main steps of one embodiment of the invention.

A method allowing the vector F(r), such as defined above, to be estimated at various radial coordinates r, from the image $I_0^\lambda$ acquired by the image sensor 16, in a spectral band Δλ, will now be described. See FIG. 3.

Step 100: Acquiring an image $I_0^\lambda$ in each spectral band Δλ.

Step 110: Initializing the vector of parameters F(r). The terms from which the initial vector is composed are defined arbitrarily or depending on knowledge of the sample. This step is carried out for each radial coordinate r in question. The vectors of parameters F(r) defined in this step form a set $\mathcal{F}^1$ of vectors describing the sample 10. Each initialized vector is denoted $F^1(r)$.

Steps 120 to 160 described below are carried out iteratively, the iteration rank being denoted n. A set $\mathcal{F}^n$ of vectors $F^n(r)$ is associated with each step.

Step 120: For each radial coordinate r, from the vector of parameters resulting from step 110, or from step 150 of a proceeding iteration, determining a complex amplitude $A_{10}^{\lambda,n}(r)$ of the exposure light wave 14, in the plane of the sample. The complex amplitude may for example be determined using one of the expressions (1) to (5). Each complex amplitude $A_{10}^{\lambda,n}(r)$ forms a complex image $A_{10}^{\lambda,n}$ of the sample. To the complex image $A_{10}^{\lambda,n}$ thus determined, applying a holographic propagation operator $h_{P_{10} \to P_0}^\lambda$, so as to obtain a complex image $A_{10}^{\lambda,n}$ of the exposure light wave 14, in the detection plane, according to the expression: $A_0^{\lambda,n} = A_{10}^{\lambda,n} * h_{P_{10} \to P_0}^\lambda$ (6).

$h_{P_{10} \to P_0}^\lambda$ is a holographic propagation operator, allowing the plane of the sample $P_{10}$ to be propagated to the detection plane $P_0$, at the wavelength λ. It may be a question of a Fresnel operator, for example $$h(x, y, z) = \frac{1}{i\lambda z}e^{j2\pi\frac{z}{\lambda}}\exp\left(i\pi\frac{x^2 + y^2}{\lambda z}\right), \quad (7)$$

with r=(x,y). Generally, the holographic propagation operator models transport of the exposure light wave between at least two points that are distant from each other. In the described application, the convolution described with reference to equation (6) models transport of the exposure light wave 14 between the plane of the sample $P_{10}$ and the detection plane $P_0$.

Considering the square root of the modulus of the exposure light wave 14, an estimation $\hat{I}_0^{\lambda,n}$ of the image $I_0^\lambda$ acquired by the image sensor is obtained. Thus, $\hat{I}_0^{\lambda,n} = \sqrt{\mod(A_0^{\lambda,n})}$ (8) where mod is the operator that returns the modulus.

Step 120 is implemented for each spectral band.

Step 130: for each spectral band, comparing the image $\hat{I}_0^\lambda$ estimated in step 120 with the image $\hat{I}_0^\lambda$ acquired by the image sensor in step 100. The comparison may be expressed in the form of a difference or of a ratio, or of a squared deviation.

Step 140: Computing a validity indicator from the comparison made, in step 130, for each spectral band. The validity indicator $\epsilon_{|\mathcal{F}^n}^n$ represents the relevance of the set $\mathcal{F}^n$ of vectors $F^n(r)$ describing the sample. The index $|\mathcal{F}^n$ means that the validity indicator is established for the set $\mathcal{F}^n$ of vectors $F^n(r)$. In this example, the validity indicator decreases as the set $\mathcal{F}$ describes the sample more correctly.

The validity indicator $\epsilon_{|\mathcal{F}^n}^n$ comprises an error criterion $\epsilon_{0|\mathcal{F}^n}^n$, the latter quantifying an overall error in the estimated image $\hat{I}_0^{\lambda,n}$ with respect to the measured image $I_0^\lambda$. By overall error, what is meant is an error for each radial coordinate and for each spectral band in question.

The error criterion $\epsilon_{0|\mathcal{F}^n}^n$ is established on the basis of the comparison of the images $\hat{I}_0^{\lambda,n}$ and $I_0^\lambda$. For example, $$\epsilon_{0|\mathcal{F}^n}^n = \frac{1}{N_r N_\lambda} \int dr \sum_\lambda \left( \frac{I_0^\lambda(r) - \hat{I}_0^{\lambda,n}(r)}{\sigma(I_0^{\lambda,n}(r))} \right)^2, \quad (10)$$

where:

$N_r$ is the number of radial coordinates in question;
$N_\lambda$ is the number of spectral bands in question;
$\sigma$ is the standard-deviation operator, enabling a noise model to be taken into account.

The index $0|\mathcal{F}^n$ attributed to the error criterion $\epsilon_{0|\mathcal{F}^n}^n$ represents the fact that this indicator is computed in the detection plane, for the set $\mathcal{F}^n$ of vectors taken into account in the iteration.

The error criterion $\epsilon_{0|\mathcal{F}^n}^n$ is a data-consistency criterion, in the sense that its minimization allows the measured data, in the present case each image $I_0^\lambda$, to be got closer to. Thus, when $\hat{I}_0^{\lambda,n}$ tends toward $I_0^\lambda$, i.e. when the set $\mathcal{F}^n$ of vectors correctly describes the sample 10, $\epsilon_{0|\mathcal{F}^n}^n$ tends toward 1. Specifically, on account of the noise, the term $$\left( \frac{I_0^\lambda(r) - \hat{I}_0^{\lambda,n}(r)}{\sigma(I_0^{\lambda,n}(r))} \right)^2$$

tends towards 1.

Taking into account the Anscombe transform, and considering the image $I_0^\lambda$ to be affected by Poisson noise $$\hat{M}_0^{\lambda,n} = \sqrt{\hat{I}_0^{\lambda,n} + \frac{3}{8}} \text{ and} \quad (11)$$

$$M_0^\lambda = \sqrt{I_0^\lambda + \frac{3}{8}} \quad (11')$$

where $\hat{M}_0^{\lambda,n}$ and $M_0^\lambda$ correspond to the moduli of the images $\hat{I}_0^{\lambda,n}$ and $I_0^n$, respectively.

Expression (10) then becomes:

$$\epsilon_{0|\mathcal{F}^n}^n = \frac{4}{N_r N_\lambda} \int dr \sum_\lambda \left( \hat{M}_0^{\lambda,n} - M_0^\lambda \right)^2 \quad (12)$$

as, because of this transform, the standard deviation is transformed into a constant deviation of value ½.

According to one embodiment, $\epsilon_{|\mathcal{F}^n}^n = \epsilon_{0|\mathcal{F}^n}^n$ (13): the validity indicator takes into account only the error criterion.

In another embodiment, detailed below, the validity indicator also comprises a morphological criterion, allowing geometric or optical constraints on the sample or on the particles forming the sample to be taken into account.

Step 150: Updating the vectors $F^n(r)$ while minimizing the validity indicator $\epsilon_{|\mathcal{F}^n}^n$. The validity indicator $\epsilon_{|\mathcal{F}^n}^n$ is a scalar variable. However, it depends on the set $\mathcal{F}^n$ of vectors of parameters on the basis of which it was established, by way of the image $\hat{I}_0^{\lambda,n}$ estimated for each spectral band in question.

In step 150, a minimization algorithm, of gradient-descent type, is applied so as to gradually approach, in each iteration, the set $\mathcal{F}^n$ allowing a satisfactory minimisation of the validity indicator $\epsilon_{|\mathcal{F}^n}^n$. Thus, the objective of this step is to establish a set $\mathcal{F}^{n+1}$ of vectors $F^{n+1}(r)$ aiming to obtain, following a reiteration of steps 110 to 140, a validity indicator $\epsilon_{|\mathcal{F}^n}^n$ that is lower than the validity indicator $\epsilon_{|\mathcal{F}^n}^n$ of the current iteration.

This step allows at least one term $F_w^n(r)$ of each vector $F^n(r)$ to be updated.

To do this, a gradient $G_w^n(r)$ of the validity indicator $\epsilon_{|\mathcal{F}^n}^n$ with respect to the optical parameter corresponding to the term $F_w^n(r)$ is defined, such that:

$$G_w^n(r) = \frac{\partial \epsilon_{|\mathcal{F}^n}^n}{\partial F_w^n(r)} \quad (14)$$

A gradient-descent algorithm then defines a direction $d_w^n$ and a step size of advance $\sigma_w^n$. The term $F_w(r)$ of each parameter vector is updated according to the expression: $F_w^{n+1}(r) = F_w^n(r) + d_w^n \sigma_w^n$ (15)

The gradient $G_w^n(r)$ may be defined for each term $F_w^n(r)$ of the vectors $F^n(r)$.

Step 160: reiterating steps 120 to 150, taking into account, in step 120 of the following iteration, the set $\mathcal{F}^{n+1}$ updated in step 150 of the iteration carried out last.

Steps 120 to 160 are reiterated until the value of the validity indicator $\epsilon_{|\mathcal{F}^n}^n$ is considered to be representative of a good description of the sample by the set $\mathcal{F}^n$ of vectors $F^n(r)$. Taking into account an indicator such as defined in equations (10) and (13), the iterations cease when the value of the validity indicator $\mathcal{F}$ is sufficiently low.

According to one variant, in step 140, the validity indicator $\mathcal{F}$ also takes into account a morphological criterion $\epsilon_{10|\mathcal{F}^n}^n$.

Unlike the error criterion $\epsilon_{0|\mathcal{F}^n}^n$, which is defined on the basis of data measured or estimated in the detection plane $P_0$, the morphological criterion $\epsilon_{10|\mathcal{F}^n}^n$ is defined in the plane of the sample $P_{10}$.

Generally, the morphological criterion $\epsilon_{10|\mathcal{F}^n}^n$ depends on the value of the terms of the vectors of parameters determined in step 110 or in step 150 of a preceding iteration, or of their spatial derivatives. It is representative of the morphology of the sample, such as determined from the vectors of parameters. In other words, the morphological criterion is a consistency criterion enabling consistency to be achieved with the morphological data of the sample, the latter possibly being defined by hypotheses.

The morphological criterion $\epsilon_{10|\mathcal{F}^n}^n$ may take into account a spatial derivative of the optical path difference, so as to take into account a predefined shape of a particle. For example, when the sample contains adherent cells, the predefined shape may be a hemisphere, such a particular case being shown in FIG. 2. When the sample contains floating cells, the predefined shape may be a sphere when the cells are spherical.

Generally, the morphological criterion may be expressed as follows:

$$\epsilon_{10|\mathcal{F}^n}^n = \int d\vec{r} \Sigma_k a_k (\Sigma_l b_{kl'} |O_{kl} * \Sigma_\lambda f_{kl}(F_{kl}^{\lambda,n}(r))|^2)^{n_k} \quad (16)$$

$a_k$ and $b_{kl}$ are real numbers, forming weighting factors;

$O_{kl}$ is an operator, for example an operator of the type that returns a partial spatial derivative, or a square root, or the Laplace operator.

$F_{kl}^{\lambda,n}(r)$ is a term of a vector $F^n(r)$, with which the weighting term $b_{kl}$ is associated, the term being defined at the wavelength $\lambda$.

$f_{kl}$ is a function applied to the term $F_{kl}^{\lambda,n}(r)$, for example a trigonometric function, such as a sine or cosine function, but it may also be a question of the identity function, such that $f_{kl}(F_{kl}^{\lambda,n}(r))=F_{kl}^{\lambda,n}(r)$;

$n_k$ is a real positive number, for example equal to 0.5 when it is desired to use a norm of order 1, or equal to 1 when it is desired to use a norm of order 2;

* is, in this expression, the application of the operator $O_{kl}$.

The morphological criterion is therefore, in its most general form, a weighted sum of operators that are applied to various terms of each vector $F^n(r)$. This weighted sum is integrated with respect to the various radial coordinates in question, so as to form a morphological indicator $\epsilon_{10|\mathcal{F}^n}^n$ taking the form of a scalar variable.

For example, if the complex amplitude of the exposure light wave 14 is defined using expression (1), each parameter vector contains a term $L^n(r)$ and an example of a morphological criterion is:

$$\epsilon_{10|\mathcal{F}^n}^n = \int dr \sqrt{\left(\frac{\partial L^n(r)}{\partial x}\right)^2 + \left(\frac{\partial L^n(r)}{\partial y}\right)^2} \quad (16)'$$

This criterion tends to decrease when the quantity $L^n(r)$ exhibits a minimum of oscillations, this for example being the case when the particles have a spherical or hemispherical particle morphology. The values of $L^n(r)$ the which the criterion is minimal therefore correspond to particles, for example spherical or hemispherical particles, that are isolated from one another, with a minimum of oscillation of $L^n(r)$ between the particles or on the latter.

The morphological criterion $\epsilon_{10|\mathcal{F}^n}^n$ is minimal when the vector of parameters $F^n(r)$ forming the set $\mathcal{F}^n$ describe objects meeting morphological hypotheses established beforehand.

When the validity indicator $\epsilon_{|\mathcal{F}^n}$ takes into account the morphological criterion $\epsilon_{10|\mathcal{F}^n}^n$, it may be defined in the form of a weighted sum of the error criterion $\epsilon_{0|\mathcal{F}^n}^n$ and of the morphological criterion $\epsilon_{10|\mathcal{F}^n}^n$. The expression of the validity indicator may then be, for example:

$$\epsilon_{|\mathcal{F}^n}^n = \epsilon_{0|\mathcal{F}^n}^n + \epsilon_{10|\mathcal{F}^n}^n \quad (17)$$

where $\gamma$ is a positive scalar.

The variation in $\epsilon_{|\mathcal{F}^n}^n$ for a variation in optical path $\delta L^n(r)$ may be expressed by the expression:

$$\delta \epsilon_{|\mathcal{F}^n}^n = 2 \int dr \sum_\lambda (\hat{M}_0^{\lambda,n} - M_0^\lambda) \delta \hat{M}_0^{\lambda,n} + \quad (18)$$

$$\gamma \int dr \frac{\frac{\partial L^n(r)}{\partial x}\frac{\partial L^n(r)}{\partial x} + \frac{\partial L^n(r)}{\partial y}\frac{\partial L^n(r)}{\partial y}}{\sqrt{\left(\frac{\partial L^n(r)}{\partial x}\right)^2 + \left(\frac{\partial L^n(r)}{\partial y}\right)^2}}$$

where:

$\hat{M}_0^\lambda$ is the modulus of the complex amplitude $\hat{A}_0^\lambda$ estimated in the plane of the sample;

$\delta \hat{M}_0^\lambda$ is a variation in the modulus $\delta \hat{M}_0^\lambda$ under the effect of a variation $\delta L(r)$ in the optical path at each radial coordinate r.

It is possible to show that:

$$G_w^n(r) = \quad (19)$$

$$\frac{\partial \epsilon_{0|\mathcal{F}}^n}{\partial L(r)} = 4\pi \text{Im} \sum_\lambda \left( \left( \left( B^\lambda(r) \left(1 - \frac{M_0^{\lambda,n}}{\hat{M}_0^\lambda}\right) \right) A_0^{\lambda,n} \right) * h_{P_{10} \to P_0}^\lambda \cdot \frac{A_{10}^{\lambda,n}}{\lambda} - \gamma \cdot \left( \frac{\partial}{\partial x}\left(\frac{\frac{\partial L^n(r)}{\partial x}}{\epsilon_M(r)}\right) + \frac{\partial}{\partial x}\left(\frac{\frac{\partial L^n(r)}{\partial x}}{\epsilon_M(r)}\right) \right) \right),$$

where Im is an operator that returns the imaginary part.

$$\epsilon_M(r) = \sqrt{\left(\frac{\partial L^n(r)}{\partial x}\right)^2 + \left(\frac{\partial L^n(r)}{\partial y}\right)^2} \quad (19')$$

with:

The term $B^\lambda(r)$ is determined during exposure of the image sensor to the illumination of the light source without a sample placed between the light source and the image sensor.

It is thus possible to determine, in each iteration, a variation $\delta L^n(r)$, at each radial coordinate r, that induces a gradual decrease in the validity indicator $\epsilon_{|\mathcal{F}^n}^n$.

When, between two successive iterations, the validity indicator $\epsilon_{|\mathcal{F}^n}^n$ no longer decreases significantly, the iterations cease. The sample is then considered to be correctly represented by the vectors $F^n(r)$ forming the set $\mathcal{F}^n$. The iterations may also cease when a preset number of iterations is reached.

According to one embodiment, the value of the scalar $\gamma$ varies as a function of the iterations. Thus, in each iteration, a validity indicator is computed such that:

$$\epsilon_{|\mathcal{F}^n}^n = \epsilon_{0|\mathcal{F}^n}^n + \gamma^n \epsilon_{10|\mathcal{F}^n}^n \quad (20)$$

$\gamma^n$ being the value of the weighting coefficient in an iteration n.

In the first iterations, $\gamma^n$ is zero or close to zero. The validity indicator then privileges consistency with the data, by way of the error criterion $\epsilon_{0|\mathcal{F}^n}^n$. When the rank n of the iterations has increased, the value of the weighting term $\gamma^n$ is increased, so as to take the morphological criterion $\epsilon_{10|\mathcal{F}^n}^n$ into account more. In this embodiment, in first iterations, the validity indicator $\epsilon_{|\mathcal{F}^n}^n$ is computed solely from the error criterion $\epsilon_{0|\mathcal{F}^n}^n$. Next, when a slightly more precise definition of the sample is available, by virtue of the vectors $F^n(r)$, the validity indicator takes into account the morphological criterion $\epsilon_{10|\mathcal{F}^n}^n$ According to one embodiment, the vectors $F''(r)$ describing the sample 10 vary. For example, in the first iterations of steps 120 to 160, the optical path difference is considered to be independent of wavelength. Each vector $F''(r)$ therefore contains a term $L''(r)$ corresponding to the optical path difference. Subsequently, for example when the term $L''(r)$ no longer varies significantly between two successive iterations, or at the end of a set number of iterations, each vector $F''(r)$ contains as many terms $L^{\lambda,n}(r)$ as there are spectral emission bands, these terms being independent of one another. This allows the model of the sample to be refined.

According to one embodiment, in step 120, imperfections in the light source are taken into account. It is for example possible to take into account the size of the source. It is a question of considering the fact that the source is not perfectly point-like. To this end, the image estimated in the detection plane is convoluted with a convolution kernel K representing an area of the source parallel to the detection plane. Thus, $\hat{I}_0^{\lambda,n} = \sqrt{\text{mod}(A_0^{\lambda,n})} * K$ (21), where * indicates convolution.

According to one embodiment, in step 120, the spectral width $\Delta\lambda$ of each emission spectral band is taken into account. Thus, in each spectral band, the image $\hat{I}_0^{\lambda,n}$ is defined taking into account an emission coefficient $s(d\lambda)$ in an elementary spectral band $d\lambda$. The elementary spectral band $d\lambda$ corresponds to the step size of discretisation of the spectral band in question.

$$\hat{I}_0^{\lambda,n} = \int d\lambda s(d\lambda) |A_0^{\lambda+d\lambda,n} * h_{P_{10}\to P_0}^{\lambda+d\lambda}| \quad (22)$$

It is possible to consider that $A_0^{\lambda+d\lambda,n} = A_0^{\lambda,n}$, by neglecting variations in $A_0$ with $d\lambda$.

Example

An example has been carried out using a sample containing cells of A549 type placed in a sample containing a liquid culture medium, at a distance of 1400 μm from a CMOS image sensor: size of the pixels: 1.67 μm×1.67 μm-10 million pixels. The light source comprised 3 light-emitting diodes that emitted in the red, green and blue, respectively. The light source was placed at a distance of 50 mm from the sample. It was coupled to a diaphragm defining a diameter aperture of 50 μm.

Figure 4A:
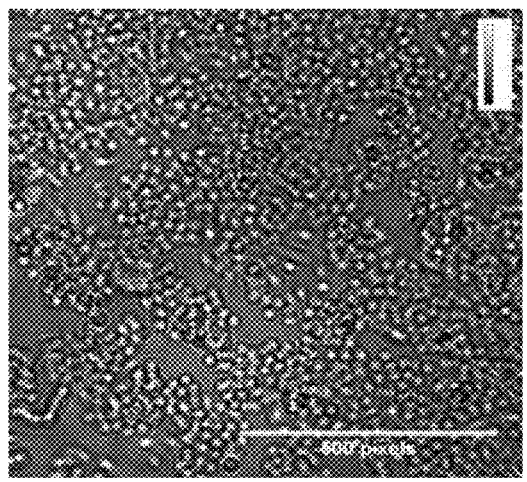
FIGS. 4A to 4E illustrates an example of implementation of the invention.
Figure 4B:
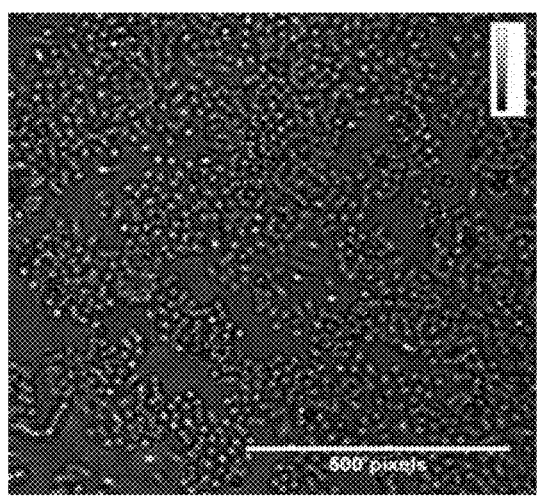
Figure 4C:
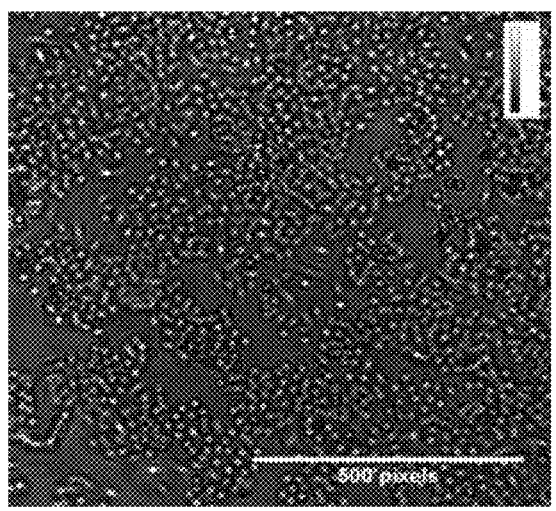

FIGS. 4A, 4B and 4C shows the images acquired in the red, green and blue spectral bands, respectively.

Figure 4D:
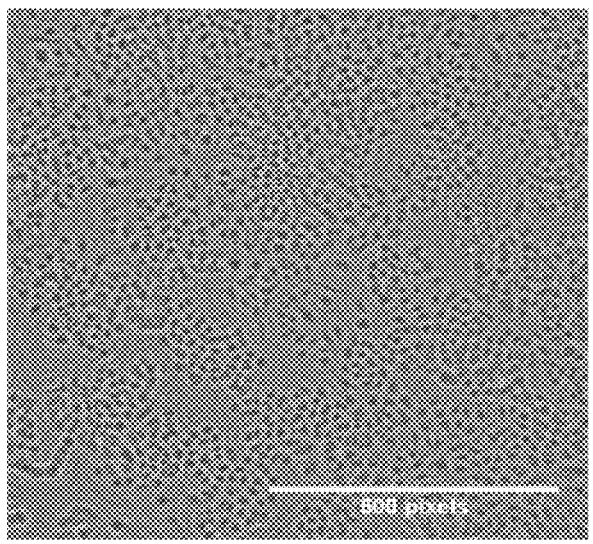

FIG. 4D shows an image of the gradient $G_w''(r)$ of the validity indicator $\epsilon_{|F^n}^n$ established for each pixel r, as a function of the parameter $L(r)$ in the first iteration (n=1). In this example, the validity indicator is such that:

$$\epsilon_{|F^n}^n = \epsilon_{0|F^n}^n + \gamma \epsilon_{10|F^n}^n \quad (24)$$

with $\epsilon_{0|F^n}^n = \dfrac{4}{N_r N_\lambda} \int dr \sum_\lambda \left(\hat{M}_0^{\lambda,n} - M_0^\lambda\right)^2$ and $\quad (25)$ $$\epsilon_{10|F^n}^n = \int dr \sqrt{\left(\dfrac{\partial L^n(r)}{\partial x}\right)^2 + \left(\dfrac{\partial L^n(r)}{\partial y}\right)^2} + \sqrt{(L^n(r))^2} \quad (26)$$

Figure 4E:
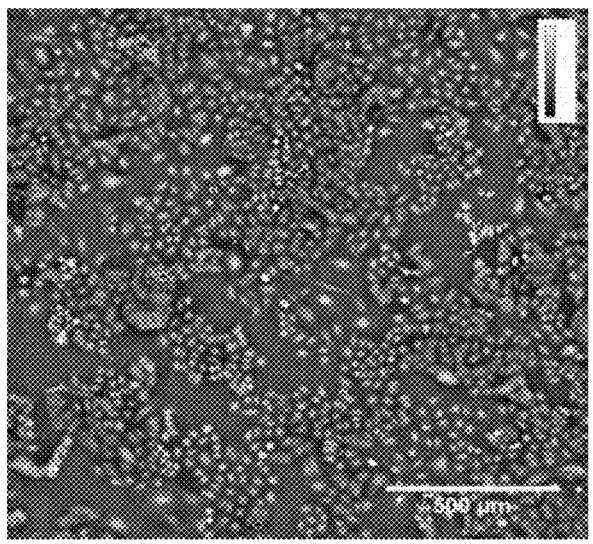

FIG. 4E shows a spatial distribution of the optical thickness $L''(r)$ in the sample on iteration n=100. This figure allows the cells to be seen and, for each thereof, a quantitative value of the optical thickness to be obtained.

Figure 5:
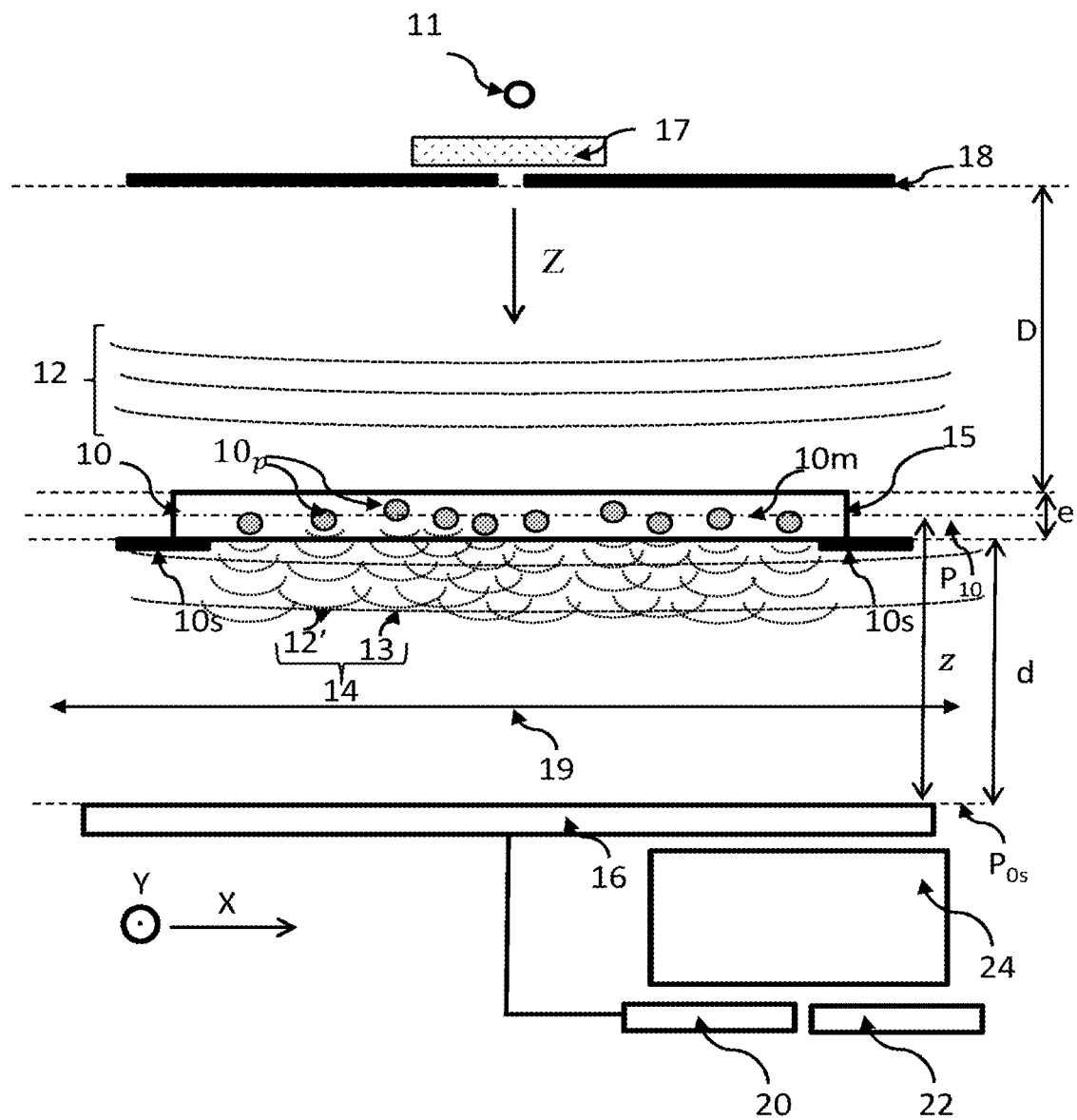
FIG. 5 shows another device allowing the invention to be implemented in a configuration called the defocused-imaging configuration.

FIG. 5 schematically shows a device allowing the invention to be implemented. Contrary to the device shown in FIG. 1A, the device of FIG. 5 comprises an optical image-forming system 19. The optical system 19 defines an image plane and an object plane. The optical system may be a lens or an objective. During the acquisition of the image of the sample, the image sensor is placed in a defocused configuration. The detection plane is offset with respect to the image plane and/or the plane in which the sample lies is offset with respect to the object plane. The offset is generally small, preferably being smaller than 1 mm, and typically lying in a range 50 μm-500 μm.

The invention will possibly be employed to observe samples in the field of biology or the health field, in the field of inspection of the environment or in other, industrial fields including the food-processing field.

The invention claimed is:

1. A method for observing a sample, the sample lying in a plane of the sample defining radial coordinates, the method comprising:
   a) illuminating the sample using a light source, configured to emit an incident light wave that propagates toward the sample along a propagation axis;
   b) acquiring, using an image sensor, an image of the sample, the image being a hologram formed in a detection plane, the sample being placed between the light source and the image sensor, such that the incident light wave sees an optical path difference, parallel to the propagation axis, by passing through the sample;
   c) processing the image acquired by the image sensor, using a processor;
   wherein the processing of the acquired image comprises:
   i) taking into account vectors of parameters, describing the sample, and respectively defined at a plurality of radial coordinates, in the plane of the sample, each vector of parameters being associated with one radial coordinate;
   ii) on the basis of the vectors of parameters, forming a complex image of the sample in the plane of the sample;
   iii) applying a holographic propagation operator to the complex image of the sample formed in the plane of the sample, and computing an image of the sample in the detection plane, said computed image being an estimation of the image of the sample acquired in b);
   iv) comparing the image of the sample acquired in b) and the image of the sample computed in iii), in order to calculate a validity indicator;
   v) updating all of the vectors of parameters, so as to make the validity indicator tend toward a preset value;
   vi) reiterating ii) to v) taking into account the vectors of parameters updated in v),
   wherein
   the method comprises, before the first iteration of step i), initializing the vectors of parameters, so that the first iteration of step i) takes into account the vectors of parameters, in the sample plane, resulting from the initialization; and
   each vector of parameters comprises a term representative of an optical path difference induced by the sample at the radial coordinate which is associated with said vector.

2. The method as claimed in claim 1, wherein v) comprises determining a gradient of the validity indicator as a function of at least one parameter, such that the vectors of parameters are updated in order to decrease the validity indicator of the following iteration.

3. The method as claimed in claim 1, wherein v) comprises implementing an algorithm of gradient-descent type.

4. The method as claimed in claim 1, wherein each parameter vector comprises:

at least one optical parameter representative of an optical path difference along the propagation axis;

an optical parameter representative of absorbance.

5. The method as claimed in claim 1, wherein v) further comprises:

taking into account a morphological constraint of the sample;

computing a morphological criterion from the vectors of parameters, the morphological criterion quantifying a deviation of the vectors of parameters, describing the sample, with respect to the morphological constraint of the sample, such that the validity indicator is obtained from a combination:

of an error criterion, determined from a comparison between the image acquired in b) and the image obtained in iii);

and of the morphological criterion.

6. The method as claimed in claim 5, wherein the validity indicator is an optionally weighted sum of the error criterion and of the morphological criterion.

7. The method as claimed in claim 6, wherein the validity indicator is a weighted sum of the error criterion and of the morphological criterion, the weighting varying between at least two successive iterations.

8. The method as claimed in claim 1, wherein:

in b), acquiring an image of the sample in various spectral bands;

each vector of parameters comprises at least one optical parameter defined in one of the spectral bands;

and wherein:

in iii), the complex image of the sample is propagated for each spectral band, so as to compute, for each spectral band, an image of the sample;

iv) comprises comparing, for each spectral band, the image computed in iii) and the image acquired in b);

such that the validity indicator computed in iv) is computed on the basis of the comparisons made in iv).

9. The method as claimed in claim 8, wherein:

in first iterations, an optical parameter is considered to not vary as a function of the spectral band;

beyond first iterations, the optical parameter is considered to be variable as a function of the spectral band.

10. The method as claimed in claim 1, wherein, in iii), the computation of the image of the sample in the detection plane comprises applying a convolution with a convolution kernel, the convolution kernel representing a spatial extent of the light source.

11. The method as claimed in claim 1, wherein, in iii), the computation of the image of the sample in the detection plane comprises an integral of an elementary image, defined in an elementary spectral band, the integral being computed to take into account an emission spectral band of the light source.

12. A device for observing a sample, comprising:

a light source, configured to emit an incident light wave that propagates toward the sample along a propagation axis in order to illuminate the sample;

a sample holder, configured to receive the sample;

an image sensor, configured to acquire an image of the sample when the sample is placed on the sample holder the image being a hologram formed in a detection plane, the sample being placed between the light source and the image sensor, such that the incident light wave sees an optical path difference, parallel to the propagation axis, by passing through the sample;

a processor, programmed to execute instructions processing the image acquired by the image sensor, wherein the processing of the acquired image comprises:

i) taking into account vectors of parameters, describing the sample, and respectively defined at a plurality of radial coordinates, in the plane of the sample, each vector of parameters being associated with one radial coordinate;

ii) on the basis of the vectors of parameters, forming a complex image of the sample in the plane of the sample;

iii) applying a holographic propagation operator to the complex image of the sample formed in the plane of the sample, and computing an image of the sample in the detection plane, said computed image being an estimation of the image of the sample acquired in b);

iv) comparing the image of the sample acquired in b) and the image of the sample computed in iii), in order to calculate a validity indicator;

v) updating all of the vectors of parameters, so as to make the validity indicator tend toward a preset value;

vi) reiterating ii) to v) taking into account the vectors of parameters updated in v), wherein the processing comprises, before the first iteration of step i), initializing the vectors of parameters, so that the first iteration of step i) takes into account the vectors of parameters, in the sample plane, resulting from the initialization; and each vector of parameters comprises a term representative of an optical path difference induced by the sample at the radial coordinate which is associated with said vector.

13. A method according to claim 1, wherein the optical path difference, at a radial coordinate, is obtained by multiplying a thickness of said sample, by the difference between a refractive index of said sample and the refractive index of a medium in which the sample lies.

14. A method according to claim 1, wherein the sample comprises particles within a medium, and wherein the optical path difference, at a radial coordinate where a particle lies, is obtained by multiplying a thickness of the particle, at said radial coordinate, by the difference between a refractive index of said particle and the refractive index of the medium.

* * * * *